(12) United States Patent
Kim et al.

(10) Patent No.: US 9,885,093 B2
(45) Date of Patent: Feb. 6, 2018

(54) L-ISOLEUCINE-PRODUCING MICROORGANISM AND METHOD OF PRODUCING L-ISOLEUCINE USING THE SAME

(71) Applicant: CJ CHEILJEDANG CORPORATION, Seoul (KR)

(72) Inventors: Hye Won Kim, Gyeonggi-do (KR); Ji Hye Lee, Gyeonggi-do (KR); Jong Hyun Kim, Gyeonggi-do (KR); Han Hyoung Lee, Seoul (KR); Ae Ji Jeon, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 46 days.

(21) Appl. No.: 14/898,099

(22) PCT Filed: Jun. 11, 2013

(86) PCT No.: PCT/KR2013/005145
§ 371 (c)(1),
(2) Date: Dec. 11, 2015

(87) PCT Pub. No.: WO2014/200126
PCT Pub. Date: Dec. 18, 2014

(65) Prior Publication Data
US 2016/0145699 A1    May 26, 2016

(51) Int. Cl.
| | | |
|---|---|---|
| *C12P 13/06* | (2006.01) | |
| *C12N 1/20* | (2006.01) | |
| *C12R 1/15* | (2006.01) | |
| *C12P 13/08* | (2006.01) | |
| *C12N 15/01* | (2006.01) | |

(52) U.S. Cl.
CPC .................. *C12R 1/15* (2013.01); *C12N 1/20* (2013.01); *C12P 13/06* (2013.01); *C12P 13/08* (2013.01)

(58) Field of Classification Search
None
See application file for complete search history.

(56) References Cited

U.S. PATENT DOCUMENTS

| | | | |
|---|---|---|---|
| 4,442,208 A | 4/1984 | Tsuchida et al. | |
| 4,656,135 A | 4/1987 | Tsuchida et al. | |
| 2002/0110876 A1 | 8/2002 | Miyata et al. | |

FOREIGN PATENT DOCUMENTS

| | | |
|---|---|---|
| JP | 61-15695 A | 1/1986 |
| KR | 10-2000-0002407 A | 1/2000 |
| KR | 10-2002-0013777 A | 2/2002 |
| KR | 10-2011-0058731 A | 6/2011 |
| KR | 10-2011-0061780 A | 6/2011 |
| KR | 10-2013-0083690 A | 7/2013 |

OTHER PUBLICATIONS

Kase et al., Agric. Biol. Chem. 41:109-116, 1977.*
Kisumi et al., "Properties of Isoleucine Hydroxamate-resistant Mutants of Serratia marcescens," Journal of General Microbiology 69: 291-297, 1971.
Park and Lee, "Fermentative production of branched chain amino acids: a focus on metabolic engineering," Appl. Microbiol. Biotechnol. 85:491-506, 2010.
Park and Lee, "Metabolic pathways and fermentative production of L-aspartate family amino acids," Biotechnol. J. 5:560-577, 2010.
Peng et al., "Combined dissolved oxygen and pH control strategy to improve the fermentative production of L-isoleucine by Brevibacterium lactofermentum," Bioprocess Biosyst. Eng. 33:339-345, 2010.
Ramos and Calderon, "Overproduction of Threonine by *Saccharomyces cerevisiae* Mutants Resistant to Hydroxynorvaline," Applied and Environmental Microbiology 58(5): 1677-1682, May 1992.
Sahm et al., "Construction of L-Isoleucine Overproducing Strains of Corynebacterium glutamicum," Naturwissenschaften 86: 33-38, 1999.
Tom and Nair, "Branched-Chain Amino Acids: Metabolism, Physiological Function, and Application. Assessment of Branched-Chain Amino Acid Status and Potential for Biomarkers," J. Nutr. 136: 324S-330S, 2006.
Wasmuth and Umbarger, "Participation of Branched-Chain Amino Acid Analogues in Multivalent Repression," Journal of Bacteriology 116(2): 562-570, Nov. 1973.
Yin et al., "Co-expression of feedback-resistant threonine dehydratase and acetohydroxy acid synthase increase L-isoleucine production in Corynebacterium glutamicum," Metabolic Engineering 14: 542-550, 2012.

* cited by examiner

*Primary Examiner* — David Steadman

(57) ABSTRACT

The present invention relates to a microorganism having an enhanced ability to produce L-isoleucine and a method of producing L-isoleucine using the same. More specifically, the present invention relates to a *Corynebacterium glutamicum* mutant strain, which is resistant to L-isoleucine and L-threonine derivatives and has an enhanced ability to produce L-isoleucine, and to a method of producing L-isoleucine using the mutant strain.

4 Claims, 1 Drawing Sheet

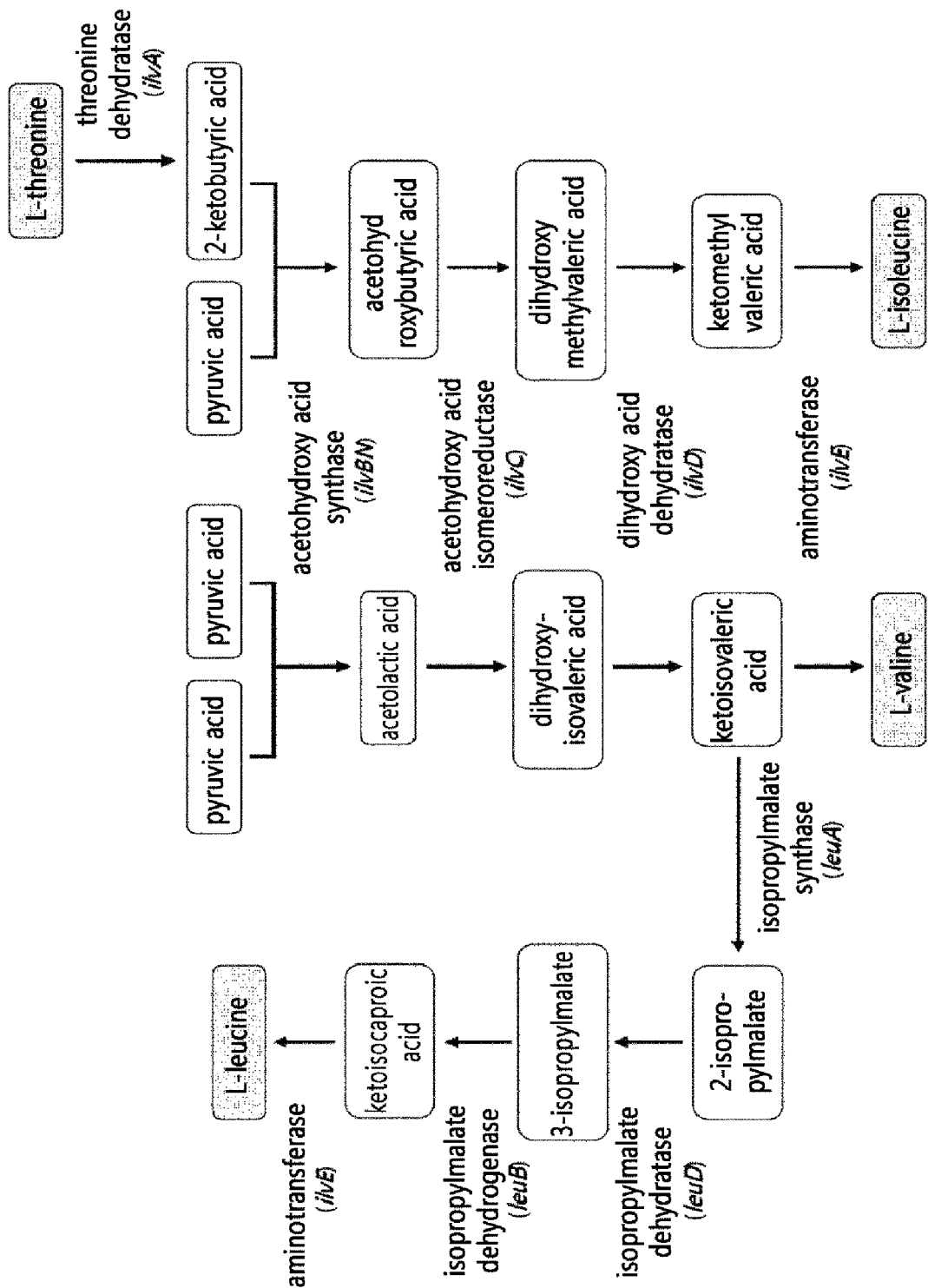

L-ISOLEUCINE-PRODUCING MICROORGANISM AND METHOD OF PRODUCING L-ISOLEUCINE USING THE SAME

CROSS-REFERENCE TO RELATED APPLICATIONS

This application is a U.S. national phase application of International PCT Patent Application No. PCT/KR2013/005145, filed Jun. 11, 2013, which application is incorporated herein by reference in its entirety.

TECHNICAL FIELD

The present invention relates to a microorganism having an enhanced ability to produce L-isoleucine and to a method of producing L-isoleucine using the same.

BACKGROUND ART

L-amino acid is the basic unit of protein and is widely used as a functional food additive and a nutrient source for animals and in the pharmaceutical industry. Among 20 amino acids, branched-chain amino acids consist of three members, L-valine, L-leucine and L-isoleucine, and the industrial value thereof is gradually increasing. It was reported that branched-chain amino acids play an important role in maintaining and forming human skeletal muscle, and functioning to regulate insulin, and maintaining and increasing muscle mass (Andrea tom et al, (2006) The journal of nutrition, 136, 324s-330s). Particularly, L-isoleucine is metabolized in muscle to produce energy and is involved in hemoglobin production, and reduces fatigue and promotes growth. Thus, it is used in various applications, including injectable fluids and nutrients, and its use in sport nutritional foods is also increasing.

To industrially produce L-isoleucine, *Corynebacterium glutamicum* is used as a representative microorganism. This microorganism produces L-isoleucine via three intermediate metabolites from pyruvate and 2-ketobutyrate as precursors (see FIG. 1). From the two precursors, 2-aceto-2-hydroxybutyrate is synthesized, and 2,3-dihydroxy-3-methylvalerate and 2-keto-3-methylvalerate are synthesized therefrom, and L-isoleucine is finally produced. To produce each of the metabolites, the enzymes acetohydroxy acid synthase, acetohydroxy acid isomeroreductase, dihydroxy acid dehydratase and aminotransferase are used (Jin Hwan Park et al, Appl microbial biotechnol, (2010) 85:491-506).

In *Corynebacterium glutamicum* strains, acetohydroxy acid synthase that is important in the L-isoleucine biosynthesis step is encoded by the ilvBN gene, and undergoes feedback inhibition by the final product L-isoleucine so that the expression of the gene and the activity of the enzyme are inhibited. In addition, threonine dehydratase that produces 2-ketobutyrate also undergoes feedback inhibition by L-isoleucine. Thus, it is known that the regulation of expression of genes and activity of enzymes involved in L-isoleucine biosynthesis are critical to generating strains that produce L-isoleucine in high yield (Jin hwan park et al, Biotechnology journal, (2010) 560-577). In addition, as can be seen in FIG. 1, L-isoleucine, L-valine and L-leucine are produced through the same biosynthesis pathway. Thus, in order to mass-produce L-isoleucine, L-threonine, that is used as a precursor of 2-ketobutyrate, should be sufficiently supplied so that the production of other branched-chain amino acids can be reduced and L-isoleucine can be continuously produced. In an attempt to solve this issue, it was reported that α-amino-β-hydroxynorvaline, an L-threonine derivative, could be used to increase the production of L-threonine (Cayo Ramos et al, Applied and environmental microbiology, (1992) 1677-1682). Further, a method of imparting L-isoleucine production ability to a microorganism having the ability to produce L-threonine (Korean Patent Laid-Open Publication No. 2011-0058731), a microorganism that produces L-threonine and L-isoleucine at the same time (Korean Patent Laid-Open Publication No. 2002-0013777), etc., were reported. Also, it was reported that the use of 4-thiaisoleucine, an isoleucine derivative, inhibited the feedback of threonine dehydratase (John J. Wasmuth, Journal of bacteriology, (1973) 562-570). Moreover, it was reported that a mutant strain resistant to isoleucine-hydroxamate has an enhanced ability to produce L-isoleucine (M. Kisumi, Journal of general microbiology, (1971) 69 291-297). In addition, there were reports of an R&D method for AHAS that comprises mutating an L-isoleucine-producing strain to increase the production of L-isoleucine compared to the production of L-valine (Korean Patent Laid-Open Publication No. 2011-0061780), and a study focused on increasing the production yield of L-isoleucine by changing the supply of oxygen, or physical conditions such as pH during fermentation (Zhihian Peng et al, Bioprocess biosyst eng, (2010) 33:339-345).

However, L-isoleucine-producing microorganisms, which have been studied and developed to date, are separately resistant to some substances in the L-isoleucine biosynthesis pathway. Thus, there still remains a need to develop an L-isoleucine-producing microorganism resistant to various substances that are involved in the control of feedback in L-isoleucine biosynthesis.

DISCLOSURE

Technical Problem

The present inventors have made extensive efforts to develop superior L-isoleucine-producing microorganisms compared to prior strains, and have found that a mutant strain which is resistant to α-amino-β-hydroxynorvaline (an L-threonine derivative), 4-thiaisoleucine and isoleucine-hydroxamate (isoleucine derivatives) produces L-isoleucine in high yield, thereby completing the present invention.

Technical Solution

It is an object of the present invention to provide a *Corynebacterium glutamicum* mutant strain for producing L-isoleucine in high yield.

Another object of the present invention is to provide a method of producing L-isoleucine using the mutant strain.

Still another object of the present invention is to provide a method of producing a mutant strain for high-yield production of L-isoleucine from *Corynebacterium glutamicum*.

Advantageous Effects

The *Corynebacterium glutamicum* mutant strain of the present invention is resistant to L-isoleucine, L-threonine and their derivatives, and thus does not undergo feedback inhibition by L-isoleucine and is sufficiently supplied with L-threonine that is a precursor of L-isoleucine. Thus, it has an enhanced ability to produce L-isoleucine. Therefore, the method of producing L-isoleucine using the microorganism according to the present invention may produce L-isoleucine with high efficiency and high yield.

DESCRIPTION OF DRAWINGS

FIG. 1 shows the biosynthesis pathway of branched-chain amino acids including L-isoleucine, the final product of the present invention. As shown in FIG. 1, branched-chain amino acids are produced through the biosynthesis pathway using the same enzyme.

BEST MODE

In one aspect, the present invention provides the *Corynebacterium glutamicum* mutant strain KCCM11248P for producing L-isoleucine.

As used herein, the term "L-isoleucine" refers to one of essential amino acids and one of branched-chain amino acids with L-valine and L-leucine, and has a structural formula of $HO_2CCH(NH_2)CH(CH_3)CH_2CH_3$.

As shown in FIG. 1, in microorganisms, L-isoleucine is biosynthesized through a four-step biosynthesis process from pyruvate and 2-ketobutyrate as precursors. However, the biosynthesis steps are also commonly used in the biosynthesis of the other branched-chain amino acids (i.e., L-valine and L-leucine) and is required to be sufficiently supplied with L-threonine, a precursor required for the biosynthesis of L-isoleucine. For this reason, it is difficult to mass-produce L-isoleucine by fermentation. The mutant strain of the present invention is resistant to feedback inhibition by the final product L-isoleucine, L-threonine, and their derivatives, and thus is sufficiently supplied with a precursor of L-isoleucine. The mutant strain of the present invention is a novel microorganism having an enhanced ability to produce L-isoleucine.

Specifically, the mutant strain of the present invention may be resistant to L-isoleucine or its derivatives and L-threonine or its derivatives. More specifically, it may be resistant to L-isoleucine derivatives and L-threonine derivatives.

As used herein, the term "derivatives" refers to known compounds that may cause feedback inhibition in the biosynthesis of the final product L-isoleucine or its precursor L-threonine which may reduce the production of L-isoleucine or L-threonine. Examples of the L-isoleucine derivatives include, but are not limited to, 4-thiaisoleucine (thiaile) and isoleucine-hydroxamate (ileHx), and examples of the L-threonine derivatives include, but are not limited to, α-amino-β-hydroxynorvaline (AHV) and the like. Specifically, the mutant strain may be resistant to one or more selected from the group consisting of 4-thiaisoleucine, isoleucine-hydroxamate and α-amino-β-hydroxynorvaline. More specifically, the mutant strain may be resistant to 4-thiaisoleucine, isoleucine-hydroxamate and α-amino-β-hydroxynorvaline.

It is generally known that the biosynthesis of L-isoleucine in cells is inhibited when L-isoleucine is accumulated over a specific concentration or titer. Accordingly, the strain resistant to the derivatives is released from feedback inhibition caused by L-isoleucine, and thus has the capability to produce L-isoleucine even under conditions containing a high concentration of L-isoleucine. In an example of the present invention, the present inventors used the derivatives to select a strain that produces a high concentration of L-isoleucine. Because L-threonine is used as a precursor of 2-ketobutyric acid for producing L-isoleucine, a strain resistant to L-threonine is released from feedback inhibition caused by L-threonine so that L-threonine is sufficiently supplied thereto. For this reason, L-threonine derivatives were also used to select a strain that produces a high-concentration of L-isoleucine.

According to the present invention, a mutant strain having an enhanced ability to produce L-isoleucine is obtained by mutating a parent strain and selecting a desired strain. Herein, mutagenesis of the microorganism can be performed by various means widely known in the art and performed using one of the physical or chemical mutagenesis methods. Examples of chemical mutagenic agents in the present invention include, but are not limited to, N-methyl-N'-nitro-N-nitrosoguanidine (NTG), diethoxybutane, ethylmethane sulfonate, mustard compounds, hydrazine, and nitrites. Examples of physical mutagenic agents include, but are not limited to UV light and gamma-radiation.

In mutagenesis, a parent strain is influenced by a mutagenic agent at a proper concentration which a viable population having a specific size remains. The size may be various depending on the kind of mutagenic agent and depends on the amount of mutation in the viable population, which is caused by the mutagenic agent at a specific kill rate. For example, when NTG is used, about 10-50% of the starting population may be remained. When mutagenesis is performed by nitrite, about 0.01-0.1% of the starting population may be remained, and when mutagenesis is performed by UV light, about 1.0% of the starting population may be remained. In an example of the present invention, in order to construct a mutant strain having an enhanced ability to produce L-isoleucine, NTG was used to induce a mutation in a parent strain.

In an example of the present invention, in order to construct a mutant strain having an enhanced ability to produce L-isoleucine, glutamate-producing *Corynebacterium glutamicum* KFCC 11040 (*Corynebacterium glutamicum* KFCC 11040 (Korean Patent Laid-Open Publication 2000-0002407) was used as a parent strain. After random mutagenesis in the parent strain was performed, the parent strain was spreaded on a minimal medium supplemented with the L-isoleucine derivatives such as 4-thiaisoleucine (thiaile) and isoleucine-hydroxamate (ileHx) and the L-threonine derivative such as α-amino-β-hydroxyvaline (AHV). The mutant strain resistant to all of the derivatives at concentrations of 1 mM, 1 mg/ml and 25 mg/ml, respectively, was selected and named "KCJI-38". In addition, it was shown that the production of L-isoleucine in the mutant strain was at least 13 times higher than that in the parent strain (see Table 1). The mutant *Corynebacterium glutamicum* strain (*Corynebacterium glutamicum*, KCJI-38) was deposited with the Korean Culture Center of Microorganisms (address: Yurim Building, 361-221, Hongje 1-dong, Seodaemun-gu, Seoul, Korea), an international depository authority, on Jan. 9, 2012 under the accession number KCCM11248P.

In another aspect, the present invention provides a method for producing L-isoleucine, the method comprising culturing the mutant strain.

Specifically, the method for producing L-isoleucine may further comprise recovering L-isoleucine from the culture medium of the mutant strain.

As used herein, the term "culturing" means allowing microorganisms to grow under artificially controlled suitable environmental conditions. In the present invention, the method of culturing the mutant *Corynebacterium glutamicum* strain to produce L-isoleucine may be performed using any *Corynebacterium glutamicum* culture method known in the art. Examples of the culture method include, but are not limited to, batch culture, continuous culture and fed-batch culture. These culture methods are disclosed in, for example, "Biochemical Engineering" (James M. Lee, Prentice-Hall International Editions, (1991) pp 138-176).

A method that is used in the culturing should satisfy the requirements for a specific strain. Culture media for *Corynebacterium glutamicum* are known (for example, Manual of Methods for General Bacteriology. American Society for Bacteriology. Washington D.C., USA, 1981).

Carbon sources that may be used in the present invention may include sugars and carbohydrates such as glucose, sucrose, lactose, fructose, maltose, starch and cellulose; oils and fats such as soybean oil, sunflower oil, castor oil and coconut oil; fatty acids such as palmitic acid, stearic acid and linoleic acid; alcohols such as glycerol and ethanol; and organic acids such as acetic acid. These substances may be used alone or in a mixture of two or more, but it's no limited thereto. Nitrogen sources that may be used in the present invention may include peptone, yeast extract, meat extract, malt extract, corn steep liquor, defatted soybean cake, and urea and inorganic compounds, such as ammonium sulfate, ammonium chloride, ammonium phosphate, ammonium carbonate and ammonium nitrate. These nitrogen sources may also be used alone or in a mixture of two or more, but it's no limited thereto. Phosphorus sources that may be used in the present invention may include potassium phosphate monobasic, potassium phosphate dibasic and corresponding sodium-containing salts. Also, the culture medium may further contain a metal salt such as magnesium sulfate or iron sulfate. In addition to the above-described substances, the medium may contain essential growth factors such as amino acids and vitamins. Additionally, the culture medium may contain suitable precursors. These substances may be added to the medium during culturing in a batch or continuous manner.

Basic compounds such as sodium hydroxide, potassium hydroxide or ammonia, or acidic compounds such as phosphoric acid or sulfuric acid may be added to the culture medium in a suitable manner to adjust the pH of the culture medium. In addition, during culture, an anti-foaming agent such as fatty acid polyglycol ester may be used to suppress the formation of bubbles. Further, in order to maintain the culture medium in an aerobic state, oxygen or oxygen-containing gas (e.g., air) may be injected into the culture medium. The culture medium may be typically maintained at a temperature ranging from 20° C. to 45° C. Culturing process of the microorganism may be continued until the desired level of L-isoleucine will be obtained. For the purpose of the present invention, the culture period may be generally 10-100 hours. L-isoleucine may be released into the culture medium or contained in cells. The method of producing L-isoleucine of the present invention comprises recovering L-isoleucine from the culture medium or the cells. Recovering L-isoleucine from the culture medium or the cells may be performed using any method known in the art, for example, centrifugation, filtration, anion exchange chromatography, crystallization or HPLC, but is not limited thereto. In an example of the present invention, the culture medium was centrifuged at low speed to remove biomass, and the supernatant was separated by high-performance liquid chromatography.

In one aspect, the present invention provides a method for producing a mutant *Corynebacterium glutamicum* strain for producing L-isoleucine, the method comprising selecting a mutant strain resistant to L-isoleucine derivatives and L-threonine derivatives from *Corynebacterium glutamicum*.

The parent strain *Corynebacterium glutamicum* may be a wild-type or mutant strain.

Specifically, the mutant strain may be obtained by a mutagenesis method.

Herein, the L-isoleucine derivatives, the L-threonine derivatives and the mutagenesis method are as described above.

The method for producing the mutant strain of the present invention may be performed by selecting a mutant *Corynebacterium glutamicum* strain, which is resistant to L-isoleucine derivatives and L-threonine derivatives and has an ability to produce L-isoleucine in a higher yield than that of conventional strains.

In still another aspect, the present invention provides the use of mutant *Corynebacterium glutamicum* strain KCCM11248P for production of L-isoleucine.

Mode for Invention

Hereinafter, the present invention will be described in further detail with reference to examples. It is to be understood, however, that these examples are for illustrative purposes and are not intended to limit the scope of the present invention.

EXAMPLE 1

Selection of Mutant Strain by Artificial Mutagenesis

In order to obtain a mutant strain having an enhanced ability to produce L-isoleucine, a mutation in a microorganism was induced in the following manner.

Specifically, the parent strain *Corynebacterium glutamicum* KFCC 11040 (Korean Patent Laid-Open Publication No. 2000-0002407) was cultured in an activating medium for 16 hours, and the activated strain was inoculated in a seed medium sterilized at 121° C. for 15 minutes. The inoculated strain was cultured for 14 hours, and 5 ml of the culture medium was collected. The collected culture medium was washed with 100 mM citric buffer, and then NTG (N-methyl-N'-nitro-N-nitrosoguanidine) was added thereto to a final concentration of 200 mg/l. Next, the culture medium was allowed to stand for 20 minutes, and then washed with 100 mM phosphate buffer. The NTG-treated strain was plated on a minimal medium, and as a result, the kill rate thereof was determined to be 85%. In order to obtain a mutant strain resistant to 4-thiaisoleucine (thiaile), isoleucine-hydroxamate (ileHx) and α-amino-β-hydroxyvaline (AHV), the NTG-treated strain was plated on a minimal medium supplemented with thiaile, ileHx and AHV to final concentrations of 1 mM, 1 mg/ml and 25 mg/ml, respectively. Then, the strain was cultured at 30° C. for 5 days, thereby obtaining a mutant strain resistant to thiaile, ileHx and AHV.

The obtained mutant strain was named "*Corynebacterium glutamicum*, KCJI-38" and deposited with the Korean Culture Center of Microorganisms on Jan. 9, 2012 under the accession number KCCM11248P.

The compositions of the media used in Examples 1 and 2 are as follows.

Activating Medium

1% meat extract, 1% polypeptone, 0.5% sodium chloride, 1% yeast extract, 2% agar, pH 7.2.

Seed Medium

5% glucose, 1% bactopeptone, 0.25% sodium chloride, 1% yeast extract, 0.4% urea, pH 7.2.

Minimal Medium 1.0% glucose, 0.4% ammonium sulfate, 0.04% magnesium sulfate, 0.1% potassium phosphate monobasic, 0.1% urea, 0.001% thiamine, 200 µg/L biotin, 2% agar, pH 7.2.

EXAMPLE 2

Examination of L-Isoleucine Productivity of L-Isoleucine-Producing Mutant Strain In order to examine the L-isoleucine productivity of the mutant strain *Corynebacterium glutamicum* KCJI-38 (KCCM11248P) resistant to thiaile, ileHx and AHV, obtained in Example 1, the strain was cultured in the following manner.

Each of the parent strain and the mutant strain was inoculated in a 250-ml corner-baffled flask containing 25 ml of a production medium, and then was cultured at 30° C. for hours with shaking at 200 rpm, thereby producing L-isoleucine.

The composition of the production medium used in Example 2 is as follows.

Production Medium

10% glucose, 0.2% yeast extract, 1.6% ammonium sulfate, 0.1% calcium phosphate monobasic, 0.1% magnesium sulfate heptahydrate, 10 mg/l iron sulfate heptahydrate, 10 mg/l manganese sulfate monohydrate, 200 µg/l biotin, pH 7.2.

After completion of the culture, the production of L-isoleucine was analyzed by high-performance liquid chromatography. The concentration of L-isoleucine in the culture product of each of the strains is shown in Table 1 below.

TABLE 1

Comparison of L-isoleucine productivity between parent strain and KCJI-38 (KCCM11248P)

| | *Corynebacterium glutamicum* KFCC 11040 (parent strain) | *Corynebacterium glutamicum* KCJI-38 (mutant strain) |
|---|---|---|
| L-isoleucine concentration (g/l) | 0.1 | 1.3 |

As can be seen in Table 1 above, the parent strain *Corynebacterium glutamicum* KFCC 11040 (Korean Patent Laid-Open Publication No. 2000-0002407) produced L-isoleucine at a concentration of 0.1 g/l, whereas the mutant strain *Corynebacterium glutamicum* KCJI-38 (KCCM11248P) produced L-isoleucine at a concentration of 1.3 g/l, suggesting that the L-isoleucine productivity of the mutant strain was about 13 times higher than that of the parent strain.

The above-described results indicate that the mutant strain resistant to L-isoleucine derivatives and L-threonine derivatives does not undergo feedback inhibition by L-isoleucine and can be sufficiently supplied with L-threonine as a precursor of L-isoleucine, suggesting that the mutant strain can produce L-isoleucine with high efficiency and high yield.

The invention claimed is:

1. An isolated *Corynebacterium glutamicum* mutant strain, wherein the isolated mutant strain has Korean Culture Center of Microorganisms (KCCM) accession number KCCM11248P.

2. A method for producing L-isoleucine comprising culturing the isolated mutant strain of claim 1 in a culture medium under suitable conditions for the production of L-isoleucine.

3. The method according to claim 2, further comprising recovering the L-isoleucine from the culture medium or the strain of the isolated mutant strain.

4. The method according to claim 2, wherein the culturing is performed at a temperature of 20-45° C. under aerobic conditions for 10-160 hours.

* * * * *